United States Patent [19]

Nowacki et al.

[11] Patent Number: 4,796,614
[45] Date of Patent: Jan. 10, 1989

[54] COLLAPSIBLE INHALATION VALVE

[75] Inventors: Christopher Nowacki, Arlington Heights; Alfred G. Brisson, Kildeer, both of Ill.

[73] Assignee: Trutek Research, Inc., Lake Zurich, Ill.

[21] Appl. No.: 19,212

[22] Filed: Feb. 26, 1987

[51] Int. Cl.[4] ............................................. A61M 11/00
[52] U.S. Cl. ........................... 128/200.14; 128/200.23; 239/338; 239/587
[58] Field of Search ....................... 128/200.14, 200.23, 128/200.15, 200.16, 200.21, 203.15, 203.23, 203.24; 222/402.12, 402.13; 239/338, 587, 427, 428.5, 432, 337, 340

[56] References Cited

U.S. PATENT DOCUMENTS

| | | | |
|---|---|---|---|
| 3,506,004 | 4/1970 | Mann et al. | 222/402.13 |
| 3,994,421 | 11/1976 | Hansen | 222/402.13 |
| 4,130,116 | 12/1978 | Cavazza | 128/200.23 |
| 4,292,966 | 10/1981 | Mono et al. | 128/200.23 |
| 4,534,343 | 8/1985 | Nowacki et al. | 128/200.23 |
| 4,641,644 | 2/1987 | Andersson et al. | 128/200.23 |

Primary Examiner—Edward M. Coven
Assistant Examiner—J. P. Lacyk
Attorney, Agent, or Firm—Robert M. Wolters

[57] ABSTRACT

A collapsible inhalation valve is provided for administering asthmatic medication or the like. The valve comprises an upright cylindrical air chamber adapted to be held in the hand. A reciprocating member holds a pressurized cartridge of medication for reciprocation between storage position substantially within the air chamber and raised using position substantially exterior to the air chamber. A mouthpiece is pivoted on the air chamber and is movable between storage position substantially within the air chamber and using position projecting from the air chamber. A one-way valve is provided at the bottom of the air chamber to allow movement of air into the air chamber while preventing movement of medication out of the air chamber. Another one-way valve is provided at the entrance to the mouthpiece permitting inhaling of misted medication, but preventing exhaling into the air chamber.

6 Claims, 2 Drawing Sheets

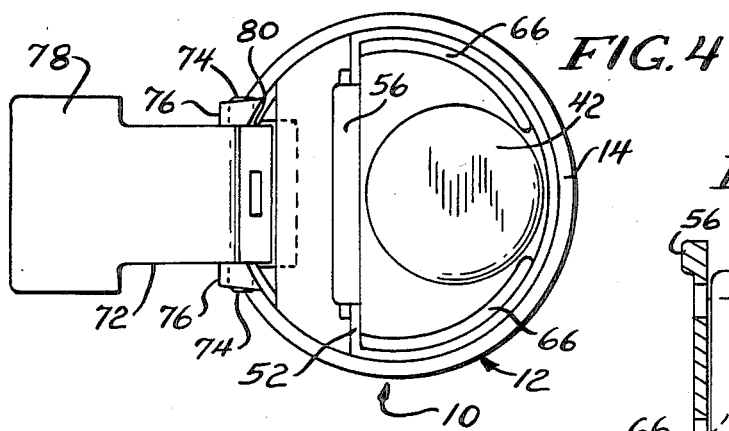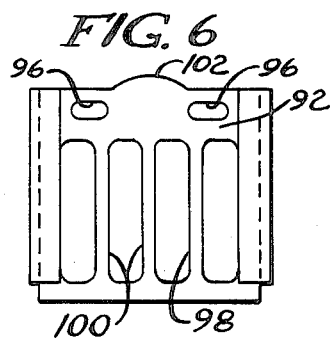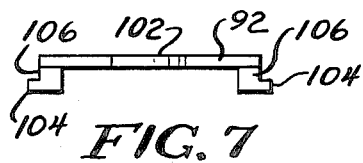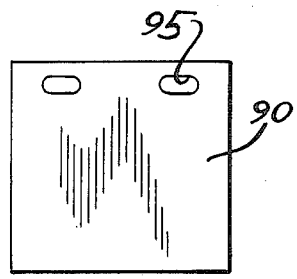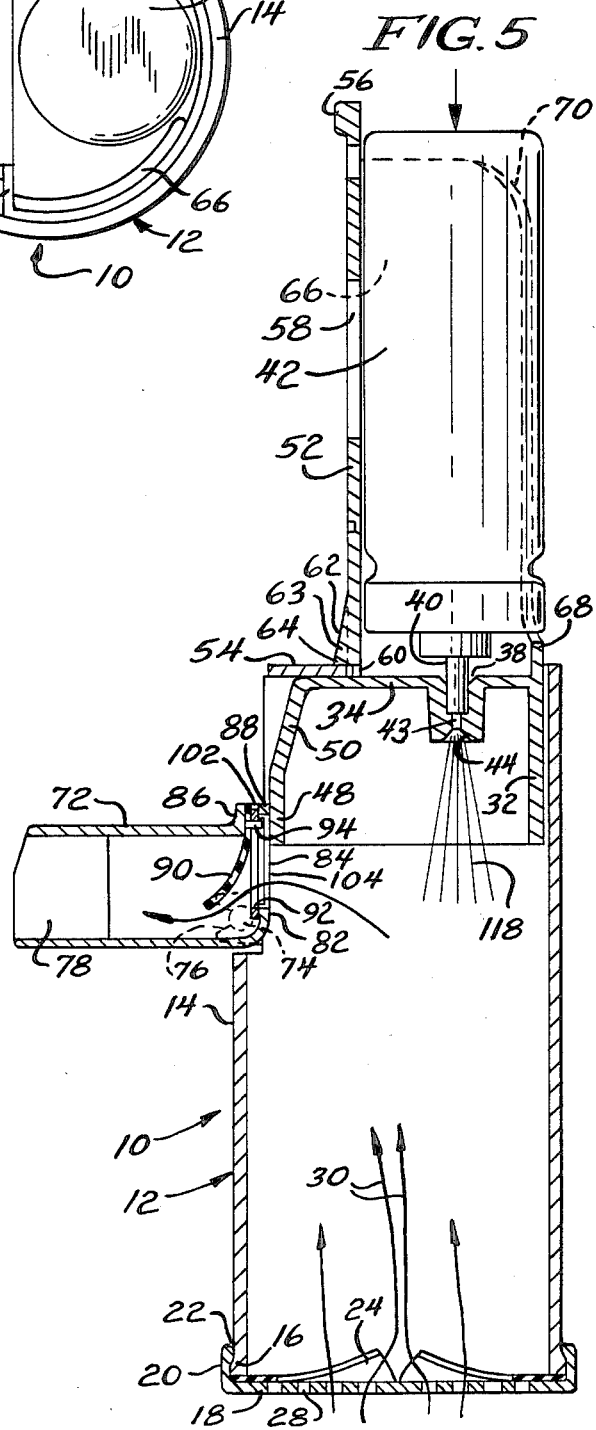

COLLAPSIBLE INHALATION VALVE

BACKGROUND OF THE INVENTION

A person suffering from asthma may when suffering an asthmatic attack have rather considerable trouble in breathing, due to swelling in the bronchii and due to secretion of mucous. There are various antiasthmatic pills that are effective, but which generally are somewhat slow acting. There are also medications available for intravenous treatment which work quite rapidly, but which require administration by skilled medical personnel. For most patients the promptest, immediately-available relief is by way of an inhalant. Epinephrine or other suitable asthmatic medication is packaged with a suitable diluent in a small pressurized canister or cartridge which interfits with the mouthpiece. The patient places the mouthpiece in his mouth, and depresses the cartridge, thereby releasing a measured amount of medication which is inhaled through the mouthpiece.

Some patients do not inhale properly, and the mouthpiece may not be completely effective in cooperation with the cartridge to convert the medication into a mist which is deposited in the proper bronchial area to relieve the asthmatic attack. Often there are small droplets, rather than a mist, and this may be compounded by improper inhalation which results in much of the medication simply going into the throat and stomach where it is ineffective against the asthmatic attach.

In our prior U.S. Pat. No. 4,470,412 for "Inhalation Valve" assigned to the same assignee, Trutek Research, Inc., we provided a cylindrical chamber with a one-way valve diaphragm to be held conveniently in the hand. The previous mouthpiece is inserted into the entering end of the inhalation valve, and the opposite end is received in the patient's mouth. This inhalation valve effects a much greater efficiency in converting the medication into a mist which does the most good.

In our subsequent U.S. Pat. No. 4,534,343 for "Metered Dose Inhaler", also assigned to the same assignee, Trutek Research, Inc., we provided an upright cylindrical chamber conveniently held in one hand. An extension cylinder at the top supports a pressurized canister of broncho-dilator medication which upon manual depression dispenses a measured dose of medication. A diffuser is provided beneath the valve of the canister for improved dispersion of the medication, thus to form very small droplets and mist within the chamber. A one-way valve is provided at the bottom of the chamber to prevent exiting of the medication from the bottom, while permitting entrance of ambient air upon inhalation. A horizontally disposed mouthpiece and one-way valve are disposed adjacent the upper margin of the chamber. Following a short time delay after operation of the canister for discharge of medication, the patient inhales through this mouthpiece, and both one-way valves open, admitting air at the bottom of the chamber as the mist is withdrawn through the horizontal mouthpiece. A reversal of flow and a swirling action are produced which effect a particularly efficient misting of the medication.

OBJECTS AND SUMMARY OF THE INVENTION

It is an object of the present invention to provide a collapsible inhalation valve having the advantages of our prior U.S. Pat. No. 4,534,343 but being collapsible to require a minimum of storage or carrying space.

More particularly, it is an object of the present invention to provide a collapsible inhalation valve having a mouthpiece pivoted between storage and using position, and having a medication canister holder which telescopes within the body of the device.

In carrying out the foregoing and other objects and advantages of the present invention, we provide a cylindrical body or chamber having a vertical axis and of a proper size to be held conveniently in the hand. A holder for a medication canister telescopes within the chamber for storage or transport, and moves axially outwardly from the chamber into operating position. A mouthpiece is provided adjacent the top of the chamber and is pivotally mounted for recessing within the chamber for storage or transport, or which extends laterally from the chamber for use. A one-way valve is provided at the bottom of the chamber for entrance of air while preventing exit of medication, and another one-way valve is provided at the entrance of the mouthpiece to permit inhalation of medication while preventing exhalation through the device with resulting loss of medication.

THE DRAWINGS

The present invention will best be understood with reference to the following specification when taken in connection with the accompanying drawings wherein:

FIG. 4 is a top view thereof with the parts in extended, using position;

FIG. 5 is a side view in longitudinal section similar to FIG. 2 but showing the parts in extended, using position;

FIG. 6 is a view of the apertured plate forming a part of the one-way valve at the entrance to the mouthpiece;

FIG. 7 is a top view of the plate of FIG. 6; and

FIG. 8 is a front view of the flexible flap or diaphragm forming a part of the valve at the entrance to the mouthpiece.

DETAILED DESCRIPTION OF THE ILLUSTRATED EMBODIMENT

Figures 1, 2:
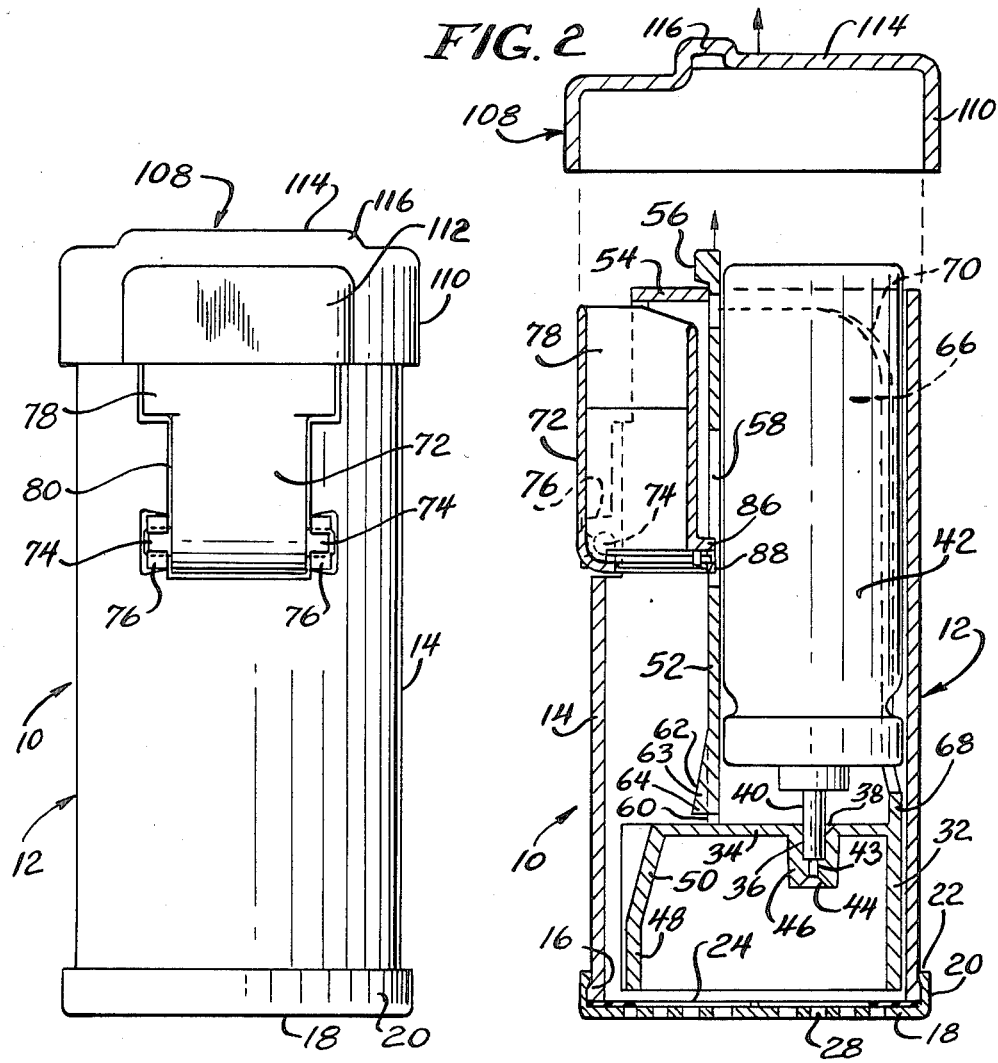
FIG. 1 is a front view of the collapsible inhalation valve in position for storage.
FIG. 2 is a side view in longitudinal section of the collapsible inhalation valve in storage position, but with the lid removed.
Figure 3:
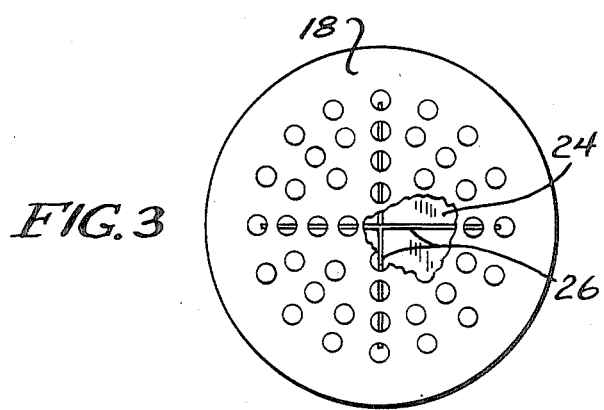
FIG. 3 is a bottom view of the collapsible inhalation valve.

A collapsible inhalation valve 10 constructed in accordance with the principles of the present invention is shown in collapsed or storage position in FIGS. 1 and 2, and in extended, using position in FIGS. 4 and 5. The collapsible inhalation valve includes a molded plastic air chamber 12 of upright cylindrical construction and of proper size and shape to fit a human hand. The chamber 12 includes a cylindrical sidewall 14 which is open at the bottom and which is mostly open at the top. The sidewall is provided adjacent the lower end with a peripheral enlargement 16. A perforated disc 18 closes the lower end, and includes a short cylindrical flange 20 with an inwardly directed circumferential enlargement 22. The flange and enlargement 22 snap over the peripheral enlargement 16 on the sidewall 14. A thin, elastomeric or plastic diaphragm 24 lies on the upper surface of the perforated disc 18 and is trapped at its periphery between the upper surface of the disc and the lower end of the sidewall 14. The diaphragm is provided with slits 26 which extend diametrally of the diaphragm nearly from edge-to-edge thereof, and which are illustrated as being at right angles from one another. The perforated disc backs up the diaphragm in a downwardly flow direction so that air cannot pass out from the chamber 12 through the perforations 28 of the disc 18. However, the diaphragm is not backed up on the upper side, and the diaphragm therefore deflects upwardly, opening at the slits 26 as shown in FIG. 5, to admit upwardly moving air as indicated by the arrows 30.

An axially movable cylinder 32 of limited axial extent is shown within the bottom of the cylindrical air chamber 12 in FIG. 2. The cylinder 32 is provided with a horizontal, flat upper wall 34 having an axial bore 36 therethrough. The axial bore is tapered outwardly at the upper end at 38, and is of a proper diameter to receive the plastic tube or nipple 40 extending from the end of a cartridge 42 of anti-asthmatic medication. The bore is restricted at 43 through approximately its lower half to limit downward movement of the nipple 40, and the bore flares outwardly at 44 at its lower extremity. A downward boss or extension 46 from the flat wall 34 accommodates the bore.

The left side of the cylinder 32 (as viewed in FIG. 2) is relieved by a flat wall 48, which tapers inwardly adjacent its upper end at 50.

A flat, chordal wall 52 extends upwardly from the horizontal wall 34 past a partial upper wall 54 on the air chamber 12, which may be integral or cemented in place. An enlargement 56 at the upper end of the wall 52 overlies the wall 54 to limit downward movement of the wall 52 and of the cylinder 32, to avoid impingement against the diaphragm 24 and possible damage thereto. In addition, the enlargement 56 comprises a finger piece for raising of the wall 52 and attendant structure. The wall 52 is provided with an opening 58 adjacent its midsection to accommodate other structures soon to be disclosed. Centrally of the wall 52, at the bottom thereof, the wall is provided with a transverse slot 60. Immediately above this slot the wall is thickened, and is provided with an exterior taper 62, thus defining a latching tooth having a bottom, right angle shoulder 64. The wall preferably is provided with short vertical slots (not shown) at the sides of the tooth for enhanced flexibility thereof.

A pair of upstanding arcuate walls 66 extend from the lateral edges of the flat wall 52 and are integral with the horizontal wall 34. The arcuate walls are joined together at their lower edges at 68, and the top corners 70 are curved or rounded off to facilitate positioning of the cartridge 42 between the walls 66 and the wall 52 as seen in FIGS. 2, 4 and 5. As will be seen by contrasting FIGS. 2 and 5, the walls 52 and 66 and the cylinder 32 are vertically reciprocal from the lowered, storage or transport position of FIG. 2 to the usable position of FIG. 5.

A mouthpiece 72 is pivotally mounted by means of laterally extending pins 74 integral therewith and received in notches in a pair of ears 76 extending from the cylindrical sidewall 14. The mouthpiece 72 is hollow from end to end, and at the outer end is enlarged at 78 to fit within a patient's mouth comfortably. The cylindrical wall 14 is recessed at 80 in a generally T-shape to accommodate the mouthpiece in the storage position shown in FIGS. 1 and 2 in which it is folded up so as to be nearly enclosed within the air chamber 12.

The inner end of the mouthpiece 72 is best considered first in the extended position of FIG. 5. The inner end includes an upturned flange 82, and above this is a straight through opening 84. A flange 86 on the upper portion of the inner end of the mouthpiece is displaced toward the outer end of the mouthpiece from the flange 82. There is also a peripheral flange 88 which is coplanar with the flange 82.

A diaphragm 90 (see also FIGS. 6-8) made of a thin elastomer or a plastic material is secured to a valve lock plate 92 by means of pins 94 which extend through horizontally elongated apertures 95 at the top of the diaphragm 90 and a pair of similar, aligned apertures 96 at the top of the valve lock plate. The valve lock plate is provided with a plurality of vertical openings 98 to permit passage of air in one direction, the openings being separated by bars 100 which serve as backing members for the diaphragm 90. A shallow curved protuberance 102 extends upwardly from the top edge of the valve lock plate 92. Vertical edge flanges 104 extend laterally out from the plate, being spaced therefrom by spacers 106. As can be seen in FIG. 5, the flanges 104 interfit with lateral portions of the mouthpiece 72 to limit insertion of the diaphragm and plate into the mouthpiece, while the lower edge of the mouthpiece fits beyond the flange 82, and the upward extension 102 snaps in behind the flange 88.

Turning to FIG. 2, it will be seen that with the mouthpiece tipped up to storage position the flanges 88 and 86 fit into the opening 58 in the wall 52.

The collapsible inhalation valve is completed by a cap 108 having a substantially cylindrical sidewall 110 with an extension 112 to fit over the top of the air chamber and mouthpiece. The cap has a top wall which is generally flat, but which is stepped to fit over the top of the cartridge 42 and of the mouthpiece 72 and wall 54, an intermediate raised section 116 being provided to fit over the enlarged upper end of the wall 52. The cap forms a fairly tight fit so as to remain in position frictionally, yet readily removable by hand.

When it is desired to use the collapsible inhalation valve 10 the mouthpiece is pivoted out from the upright position in FIG. 2 to the extended, transverse position of FIG. 5. The enlargement 56 on the wall 52 is gripped by the fingers and raised to raise the attendant structure to the position shown in FIG. 5. This causes the tooth 63 to snap over the edge of the wall 54 to hold the cylinder 32, the wall 52, and attendant parts in raised position. When it is desired to lower these parts, it is necessary to press in against the tapered edge 62 of the tooth to deflect the tooth to clear the wall 54.

With the parts in extended or useful position, the mouthpiece 92 is placed in the mouth of the asthmatic person. The top of the cartridge 42 is depressed, and this causes a vapor mist to be expelled from the cartridge down into the air chamber as indicated somewhat schematically at 118 in FIG. 5. Passage of the diluent and medication through the orifice 42 and the flared end 44 thereof causes a certain degree of vaporization, and expansion thereof into the air chamber 12 causes further expansion. The vaporized medication cannot pass out through the bottom of the air chamber due to the diaphragm 24 which prevents outward air flow. After a short pause the patient inhales through the mouthpiece 72. This causes the valve diaphragm 90 to open as a flap valve as shown in FIG. 5, with the diaphragm 24 deflecting upwardly, whereby ambient air is drawn in to the air chamber as previously indicated at 30. This results in turbulence within the chamber and further mixing of the medication with the air as a vapor, which is drawn through the mouthpiece and into the bronchi and lungs of the user. The patient cannot exhale through the collapsible inhalation valve, since attempted exhalation would cause the flap valve diaphragm 90 to close tightly, and further since nothing can pass out through the bottom of the air chamber 12 due to the diaphragm 24 and backing thereof by the plate 18. It is contemplated that following depression of the medication canister, the patient would inhale deeply and hold his breath for several seconds, and would then exhale through his nose, or through his mouth around the mouthpiece 72. Second and subsequent inhalations then would be made to insure that all of the medication discharged into the inner chamber 12 would be inhaled.

The downward discharge of the medication into the air chamber and the lateral withdrawal thereof produces particularly efficient vaporization of the medication, generally in the same manner as in our prior U.S. Pat. No. 4,534,343. However, the inhalation valve of the present invention is improved over that patent in the provision for the storage of the medication cartridge 42 and mounting structure therefor within the air chamber, and storage of the mouthpiece 72 substantially within the air chamber.

Reference has been made heretofore to the tooth 63 which positively holds the cartridge and supporting structure in raised position. At the same time the flattened portion of the wall 48 abuts the flange 88 of the mouthpiece, so that the mouthpiece cannot be folded into storage position until after the cartridge and supporting structure have been lowered.

The specific structure as herein described will be understood as being for illustrative purposes. Various changes will no doubt occur to those skilled in the art and will be understood as forming a part of the present invention insofoar as they fall within the spirit and scope of the appended claims.

The invention is claimed as follows:

1. A collapsible inhalation valve for administering asthmatic medication or the like comprising an upright cylindrical air chamber adapted to be held in the hand and having an upper end and a lower end, means for supporting a pressurized cartridge of medication, means mounting said cartridge supporting means to said air chamber for movement between storage position substantially within said air chamber and raised using position above and substantially out of said air chamber, means for establishing fluid communication from said cartridge into said air chamber with said cartridge supporting means in said raised using position for spraying a measured dose of medication into said air chamber, a one-way valve including a diaphragm adjacent the lower end of said air chamber for admitting air but retaining medication, a mouthpiece adjacent the upper end of said air chamber for receipt in a patient's mouth, said air chamber opening into said mouthpiece to pass medication from said air chamber through said mouthpiece and into the patient upon patient inhalation, and stop means on said cartridge supporting means coacting with said air chamber to stop said cartridge means short of said diaphragm.

2. A collapsible inhalation valve as set forth in claim 1 and further including cooperating latch means on said cartridge supporting means and engageable with said air chamber to latch said cartridge supporting means with said cartridge in raised using position coaxial with its storage position.

3. A collapsible inhalation valve as set forth in claim 1 wherein the means for mounting the cartridge supporting means comprises means for permitting verticle reciprocal movement of said cartridge supporting means, said cartridge supporting means comprising a cylinder reciprocal only vertically within said air chamber, and further including means on said cartridge supporting means and engageable with said air chamber for latching said cylinder in raised position with said cartridge in raised using position.

4. A collapsible inhalation valve for administering asthmatic medication or the like comprising an upright cylindrical air chamber adapted to be held in the hand and having an upper end and a lower end, means for supporting a pressurized cartridge of medication, means mounting said cartridge supporting means to said air chamber for movement between storage position substantially within said air chamber and raised using position above substantially out of said air chamber, means for establishing fluid communication from said cartridge into said air chamber with said cartridge supporting means in said raised using position for spraying a measured dose of medication into said air chamber, a one-way valve adjacent the lower end of said air chamber for admitting air but retaining medication, a mouthpiece adjacent the upper end of said air chamber for receipt in a patient's mouth, said air chamber opening into said mouthpiece to pass medication from said air chamber through said mouthpiece and into the patient upon patient inhalation, the means for mounting the cartridge supporting means comprising means for permitting vertical reciprocal movement of said cartridge supporting means, said cartridge supporting means comprising cylinder vertically reciprocal within said air chamber, said air chamber having a top member thereon engageable by said cylinder and limiting upward movement of said cylinder, and further including latch means on said top member and said cylinder.

5. A collapsible inhalation valve for administering asthmatic medication or the like comprising an upright cylindrical air chamber adapted to be held in the hand and having an upper end and a lower end, means for supporting a pressurized cartridge of medication, means mounting said cartridge supporting means to said air chamber for movement between storage position substantially within said air chamber and raised using position above and substantially out of said air chamber, means for establishing fluid communication from said cartridge into said air chamber with said cartridge supporting means in said raised using position for spraying a measured dose of medication into said air chamber, a one-way valve adjacent the lower end of said air chamber for admitting air but retaining medication, a mouthpiece adjacent the upper end of said air chamber for receipt in a patient's mouth, said air chamber opening into said mouthpiece to pass medication from said air chamber through said mouthpiece and into the patient upon patient inhalation, and further including means pivotally mounting said mouthpiece on said air chamber whereby said mouthpiece is movable between storage position substantially within said air chamber and using position projecting out from said air chamber, said cartridge supporting means comprising a cylinder vertically movable within said air chamber, and wherein said cylinder in raised position is disposed adjacent a portion of said mouthpiece and blocks said mouthpiece against movement into storage position substantially within said air chamber.

6. A collapsible inhalation valve as set forth in claim 5 and further including latch means on said cartridge supporting means and engageable with said air chamber to latch said cartridge supporting means for latching said cartridge supporting means in raised position.

* * * * *